(12) United States Patent
Jørsboe et al.

(10) Patent No.: US 6,307,127 B1
(45) Date of Patent: *Oct. 23, 2001

(54) TRANSFORMATION OF GUAR

(75) Inventors: Morten Jørsboe, Nykøbing F; Finn T. Okkels, Roskilde, both of (DK)

(73) Assignee: Danisco A/S, Copenhagen (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,267
(22) PCT Filed: Jun. 6, 1995
(86) PCT No.: PCT/DK95/00221
§ 371 Date: Apr. 4, 1997
§ 102(e) Date: Apr. 4, 1997
(87) PCT Pub. No.: WO95/34667
PCT Pub. Date: Dec. 21, 1995

(30) Foreign Application Priority Data

Jun. 10, 1994 (DK) .................................................. 0662/94

(51) Int. Cl.$^7$ ............................. C12N 5/04; C12N 15/84; C12N 15/90; A01H 5/00
(52) U.S. Cl. ......................... 800/294; 435/419; 435/421; 435/430; 435/430.1; 435/469; 800/313
(58) Field of Search .................................. 800/278, 294, 800/298, 313; 435/252.2, 468, 469, 410, 419, 420, 421, 430, 431, 430.1; 530/412

(56) References Cited

U.S. PATENT DOCUMENTS

| | | | | |
|---|---|---|---|---|
| 4,269,975 | * | 5/1981 | Rutenberg et al. | .................. 536/114 |
| 5,565,346 |   | 10/1996 | Facciotti | ............................. 435/172.3 |
| 5,569,834 |   | 10/1996 | Hinchee, et al. | ..................... 800/205 |

FOREIGN PATENT DOCUMENTS

| | | |
|---|---|---|
| 0 561 082 | 9/1993 | (EP) . |
| 92/17598 | 10/1992 | (WO) . |
| 93/09665 | 5/1993 | (WO) . |
| 94/02620 | 2/1994 | (WO) . |

OTHER PUBLICATIONS

McCabe et al, Plant Cell, Tiss. Org. Cutt. vol. 33, pp. 227–236, 1993.*
Meicenheimer, Roger D., "Changes in epilobium phyllotaxy induced by N–1–Naphthylphthalamic acid and α–4–chlorophenoxyisobutyric acid.", Amer. J. Bot., vol. 68, No. 8, pp. 1139–1154 (1981).
Overbeeke, Nico et al., "Cloning and nucleotide sequence of the α–galactosidase cDNA from Cyamopsis tetragonoloba (guar).", Plant Molecular Biology, vol. 13, pp. 541–550 (1989).
Perl, A. et al., "Improvement of plant regeneration and GUS expression in scutellar wheat calli by optimization of culture conditions and DNA–microprojectile delivery procedures.", Mol. Gen. Genet., vol. 235, pp. 279–284 (1992).
Schroeder, Hartmut E. et al., "Transformation and regeneration of two cultivars of pea (*pisum sativum* L.)."Plant Physiol., vol. 101, pp. 751–757 (1993).
Hinchee, Maud A. W. et al., "Production of transgenic soybean plants using agrobacterium–mediated DNA transfer.", Bio/Technology, col. 6 (Aug. 1988).
Potrykus, I., Annu. Rev. Plant Physiol. Plant Mol. Biol., vol. 42, pp. 205–225, 1991.*
Saxena et al, Z. Pflanzenphysiol., vol. 106, pp. 277–280, 1982.*
Bansal et al, J. Phytol. Res., vol. 7, pp. 57–60, 1994.*
Kobayashi et al, Hortscience, vol. 29, pp. 327–328, 1994.*
Jacobs et al, Antimicrob. Agents Chemother., vol. 29, pp. 980–985, 1986.*
Horsch et al, Science, vol. 227, pp. 1229–1231, 1985.*
McCleary et al, Carboh. Res., vol. 139, pp. 237–260, 1985.*
Jowett, D., Nature, vol. 182, pp. 816–817, 1958.*
Tsang et al, Plant Cell Rep., vol. 8, pp. 214–216, 1989.*
Garcia, et al., *Transformation of Cowpea Vigna Unquiculata Cells with an Antibiotic Resistance Gene using a Ti–Plasmid–Derived Vector,* Plant Science, vol. 44, pp. 37–46, 1986.
McClean, et al., *Susceptibility of dry bean (Phaseolus vulgaris L.) to Agrobacterium infection: Transformation of cotyladonary and hypocotyl tissues,* Plant Cell, Tissue and Organ Culture, vol. 24, pp. 131–138, 1991.
Puonti–Kaerlas, et al., *Transformation of pea (Pisum sativum L.) by Agrobacterium tumefaciens,* Plant Cell Reports, vol. 8, pp. 321–324, 1989.
Voisey, et al., *Agrobacterium–mediated transformation of white clover using direct shoot organogenesis,* Plant Cell Reports, vol. 13, pp. 309–314, 1994.

* cited by examiner

*Primary Examiner*—David T. Fox
*Assistant Examiner*—Ashwin D. Mehta
(74) *Attorney, Agent, or Firm*—Iver P. Cooper

(57) ABSTRACT

The invention relates to a method for the transformation of legumes of the genus Cyamopsis, in particular Agrobacterium-mediated transformation of guar (*Cyamopsis tetragonoloba*), by introducing a recombinant DNA sequence into at least one cell or protoplast and generating genetically modified explants using at least one selection or shoot growth medium comprising at least one compound selected from an auxin inhibitor, e.g. 2-(p-chlorophenoxy)-2-methylpropionic acid (PCIB), a β-lactamase inhibitor, e.g. sulbactam, and an ethylene inhibitor, e.g. silver thiosulfate, so as to obtain genetically modified plant or part thereof containing in its genome at least one recombinant DNA sequence; to genetically modified plants produced by the method; and to the use of substances such as the β-lactamase inhibitor sulbactam to facilitate transformation of guar and other plants.

30 Claims, 2 Drawing Sheets

TRANSFORMATION OF GUAR

FIELD OF THE INVENTION

The present invention relates to a method for transformation, regeneration and selection of legumes of the genus Cyamopsis, in particular Agrobacterium-mediated transformation of guar (*Cyamopsis tetragonoloba*), to genetically modified plants produced by the method, as well as to the use of substances such as the β-lactamase inhibitor sulbactam to facilitate transformation of guar and other plants.

BACKGROUND OF THE INVENTION

Transformation of legumes

The Fabaceae (Leguminosae) family is the most important dicot plant family in the world. Because of its huge economic significance, much effort has been invested in improving agronomic traits by genetic engineering.

Agrobacterium-mediated transformation is a commonly employed method for transferring genes into plants. The plant species that until now have been successfully transformed by Agrobacterium are exclusively dicots (as opposed to monocots), but not all dicots are easily transformed.

Some plant families, for example Solanaceae, have been demonstrated to be particularly well suited for Agrobacterium-mediated gene transfer, while other families, such as the Fabaceae, are notorious for being recalcitrant.

Production of transgenic soybean plants (*Glycine max*) has been attempted in a variety of ways. Leaves and protoplasts have been used as explant sources, but no regeneration into transformed plants has been obtained in this manner. Cotyledons of soybean inoculated with *Agrobacterium tumefaciens* resulted in transgenic plants, but only one of the numerous tested genotypes was successfully transformed in this way (Hinchee et al., *Bio/Technology* 6:915, 1988). WO 94/02620 describes a method for producing transgenic soybean plants using hypocotyls or cotyledonary nodes and a series of steps specially designed for soybean transformation, including particular temperatures, pH values and Agrobacterium concentrations.

The use of cotyledons as explants is not, however, generally applicable to legume transformation, and other explant sources have been used in most cases. For example, for pea (*Pisum sativum*) transformation, explants from shoot cultures and seedling epicotyls have been employed as explants, and transgenic callus thus obtained was after 6 months regenerated to plants (Puonti-Kaerlas et al., *Plant Cell Rep.* 8:321, 1989).

For white clover (*Trifolium repens*) transformation shoot tips were inoculated with Agrobacteria, and transgenic plants were obtained (Voisey et al., *Plant Cell Rep.* 13:309, 1994).

Attempts have been made to transform a number of other legumes. For example, *Phaseolus vulgaris* cotyledonary nodes and hypocotyls incubated with *Agrobacterium tumefaciens* resulted in transgenic calli but no transgenic plants (McClean et al., *Plant Cell, Tissue & Org. Cult.* 24:131, 1991). Likewise with the genus Vigna (Garcia et al., Plant Science 48:49, 1986). No transgenic plants of peanut (*Arachis hypogaea*) have been reported despite considerable effort.

The present inventors have tried to transform guar using the soybean cotyledon procedure described by Hinchee et al., but were unsuccessful. Together with the results reported by other researchers, this demonstrates that the choice of transformation method for legumes is fully empirical, and that no general scientifically based guidelines can be deduced. Thus, the transformation procedure and explant source for transformation of a legume have to be developed according to the particular requirements of the genus, species, or even genotype, in question.

The numerous reported attempts to obtain transgenic plants of various legumes clearly show that transformation of legumes is very difficult, even to a scientist skilled in the art. This is further evidenced by the fact that of the approximately 100 legume species of commercial interest, less than 5 species have been transformed. Thus, successful transformation of a previously untransformed legume genus or species is anything other than routine.

Guar

Guar (*Cyamopsis tetragonoloba*) is a legume of significant commercial interest due to the high content of galactomannan in the seeds. Guar galactomannan is also known as guar gum and is used as an viscosity enhancer for both food and nonfood purposes.

The galactomannan is found in the endosperm, which makes up about 35% of the dry weight of the seed, 80–90% being pure galactomannan. Large endosperms are an unusual feature in Fabaceae, where the endosperm fraction of the seeds is predominantly absent or rudimentary; instead food reserves for germination in legumes are most often deposited in enlarged cotyledons.

None of the legume species with large galactomannan containing endosperms have been reported to have been genetically transformed.

Sulbactam

An inherent drawback of Agrobacterium-mediated gene transfer is the fact that the bacteria continue to grow after transformation. In order to prevent overgrowth of the plant material, the bacteria must be effectively eliminated, normally by addition of a penicillin-like antibiotic (β-lactams) such as carbenicillin, cefotaxime, etc.

The penicillin-like substances are chosen because they are in principle non-toxic to plant tissues. In practice, however, these compounds often exert a considerable toxic effect on the explants. One possible reason for the phytotoxicity, aside from possible direct toxic effects, may be that the antibiotics are gradually degraded during the long incubation time in the presence of both bacteria and plant tissues. An example of an undesirable degradation product is from the very commonly used antibiotic carbenicillin, which can be degraded to phenylacetic acid. Phenylacetic acid possesses auxin-like properties and consequently gives increased callus growth on the explant, which in turn may impair regeneration.

Thus, it would be highly desirable to be able to use smaller amounts of antibiotics and/or antibiotics that do not have such undesired side effects. In the course of their work on the transformation of guar, the inventors found that the β-lactamase inhibitor sulbactam dramatically reduces the required concentrations of penicillin-like substances, thereby improving transformation efficiency and reducing costs significantly.

This novel approach to control Agrobacteria growth is generally applicable to transformation of plants because it is related to the bacteria which must always be eliminated during transformation, and is thus not limited to any particular plant species.

SUMMARY OF THE INVENTION

In one aspect, the present invention relates to a genetically modified plant or part thereof of the genus Cyamopsis, said plant or plant part comprising in its genome at least one recombinant DNA sequence.

Another aspect of the invention relates to a method for producing a genetically modified plant or part thereof of the genus Cyamopsis, comprising the steps of introducing a recombinant DNA sequence into at least one cell or protoplast and generating genetically modified explants using at least one selection or shoot growth medium comprising at least one compound selected from an auxin inhibitor, a β-lactamase inhibitor and an ethylene inhibitor, so as to obtain a genetically modified plant or part thereof containing in its genome at least one recombinant DNA sequence.

A further aspect of the invention relates to a method for producing a genetically modified plant in which at least one medium used for selection or growth of cells, protoplasts, callus or plant parts comprises at least one substance that inhibits bacterial growth or that increases the effect of a bacterial growth inhibitor without having any substantial plant growth regulating or plant toxic effect.

In an additional aspect, the invention relates to chimeric plants capable of producing transgenic seeds and obtained by grafting a genetically modified shoot cultivated in vitro onto a non-in vitro cultivated plant.

DETAILED DESCRIPTION OF THE INVENTION

The terms "genetically modified plant" and "transgenic plant" in the context of the present application refer to the generally understood meanings of these terms in the art, i.e. plants that have been altered in such a manner that their genome comprises at least one recombinant DNA sequence. The "recombinant DNA sequence" will typically be one which is able to be expressed or which affects gene expression in the plant, but may also be e.g. a sequence that can serve as a marker, without necessarily being expressed or affecting gene expression. Sequences that are expressed or that affect gene expression will often be genes that are foreign to the plant in question in its native form, but can also be e.g. a slightly altered form of the native gene or for example a promoter or regulator sequence that results in altered expression of the native gene. The method disclosed herein for producing genetically modified plants is aimed at genetic transformation in general and is not limited to the incorporation of any particular category of DNA sequences.

The term "plant parts" refers in general to any plant part, e.g. tissue or organ, that is not a complete plant, including undifferentiated callus as well as differentiated plant parts such as shoots, leaves, roots, fruits, seeds, etc.

As indicated above, the invention relates in particular to genetically modified plants of the genus Cyamopsis, and more particularly to plants of the species *C. tetragonoloba* (guar). Genetically modified Cyamopsis plants may be produced by the method mentioned above, in which the first step is the introduction of a recombinant DNA sequence into at least one cell or protoplast. Introduction of the recombinant DNA may be achieved by methods commonly employed for the production of genetically engineered plants, including Agrobacterium-mediated transfer, e.g. by means of an *A. tumefaciens* Ti-plasmid or an *A. rhizogenes* Ri-plasmid as a vector, as well as by e.g. microinjection, electroporation or particle bombardment. A preferred method (described below in the Examples) is Agrobacterium-mediated gene transfer. As explained below, good results have been obtained by transforming cotyledons using *Agrobacterium tumefaciens*, even though the cotyledons used were from seeds that had been germinated for a relatively long period of time, such as 11–12 days.

After introduction of the desired recombinant DNA into the chosen plant material (e.g. tissue, cells or protoplasts), genetically modified explants are generated using at least one selection or shoot growth medium comprising at least one compound selected from an auxin inhibitor, a β-lactamase inhibitor and an ethylene inhibitor, since it has been found that the presence of one or more of these compounds in the selection and/or shoot growth medium leads to less callus and an increased frequency of regenerated and transformed shoots. Preferably, the selection medium comprises at least an auxin inhibitor and a β-lactamase inhibitor, and the shoot growth medium comprises at least a β-lactamase inhibitor. More preferably, the selection medium comprises an auxin inhibitor, a β-lactamase inhibitor and an ethylene inhibitor, and the shoot growth medium comprises an auxin inhibitor and an ethylene inhibitor.

The inhibitors (auxin inhibitor, β-lactamase inhibitor, ethylene inhibitor) can function either by eliminating or reducing the amount of the respective compounds (i.e. by inhibiting biosynthesis of the compounds or by degradation of the compounds) or by inhibiting the action of the compounds. While not wishing to be bound by any particular theory, it is believed that the effect of the inhibitors is, at least in part, related to anti-auxin effects or to the inhibition of "auxin-like" effects, since the presence of auxin leads to increased callus growth and therefore to a lower frequency of shoot regeneration and isolation of transformed shoots. This is obviously the case for those compounds that function directly as auxin inhibitors. As for the β-lactamase inhibitors, it was explained above by way of example that one presumed effect of sulbactam is the elimination of the degradation product phenylacetic acid (from the antibiotic carbenicillin), phenylacetic acid having undesirable auxin-like properties that result in increased callus growth. Similarly, the ethylene inhibitor, in addition to its direct effect on ethylene which presumably serves to prevent premature senescence in developing shoots, is also believed to have a beneficial influence due to the fact that ethylene is known to be associated with auxin responses. The use of an auxin inhibitor and the ethylene inhibitor will be advantageous regardless of the type of gene transfer employed, e.g. with bacteria-mediated transfer such as Agrobacterium-mediated transfer as well as other methods such as microinjection, electroporation and particle bombardment, while the use of the β-lactamase inhibitor is particularly suited to procedures employing gene transfer by means of Agrobacterium or other β-lactamase producing bacteria strains.

A preferred auxin inhibitor is 2-(p-chlorophenoxy)-2-methylpropionic acid (PCIB), which may be used in the selection medium and optionally also in the shoot growth medium in a concentration of about 0.01–10 mg/l, typically about 0.05–5 mg/l, e.g. about 0.1–2 mg/l. Other auxin inhibitors that may be used are e.g. 2,3,5-triiodobenzoic acid (TIBA), N-naphthylphthalamic acid (NPA), morphactins, 2,4,6-trichlorophenoxyacetic acid and 7-chloroindolacetic acid.

A preferred β-lactamase inhibitor is sulbactam (available from Pfizer under the trade name Betamaze). Sulbactam may be used in the selection medium or the shoot growth medium in a concentration of about 10–1000 mg/l, typically about 20–500 mg/l, e.g. about 50–200 mg/l.

A preferred ethylene inhibitor is silver thiosulfate, which is typically used in the selection or shoot growth medium in a concentration of up to about 50 μM, typically about 0.1–10 μM, e.g. about 0.5–5 μM. Other ethylene inhibitors that may be used are e.g. aminoethoxyvinyl glycine (AVG), cobalt and norborneol.

In addition to the compounds described above, certain other compounds have also been found to have a beneficial effect when used in the selection and/or shoot growth medium. For example, it has been found that an improved transformation frequency was obtained when a nickel salt was added to the selection medium. Thus, the selection medium preferably contains a nickel salt, e.g. $NiCl_2$, 6 $H_2O$, e.g. in a concentration of about 0.1–10 mg/l, for example 0.5–5 mg/l. Also benzyladenine purine (BAP) has been found to lead to an improved result. The selection medium thus preferably contains BAP, e.g. in a concentration of about 0.1–10 mg/l, such as 1–5 mg/l. BAP may also be present in the shoot growth medium in similar concentrations.

The presence of kanamycin, e.g. in the form of kanamycin sulfate in a concentration of about 50–300 mg/l, typically about 100–200 mg/l, for example about 130–160 mg/l, in the selection medium has also been shown to have a beneficial effect when the inserted DNA sequence includes a gene for kanamycin resistance. It has also been found that good results are obtained when explants, typically explants from which shoots have been harvested, are transferred to a second selection medium with a lower kanamycin concentration than that of the first selection medium, preferably not more than 125 mg/l, typically 20–100 mg/l, e.g. 30–70 mg/l. Similarly, other amino-glycoside antibiotics such as hygromycin, neomycin, streptomycin and gentamycin may also be employed in the selection medium together with an inserted DNA sequence comprising the relevant antibiotic resistance gene. Other selection agents, e.g. herbicides or positive selection agents such as mannose or xylose may also be used.

After selection and harvest of regenerated shoots, the presence of genetically transformed shoots may be determined by various methods. One of these (in addition to the use of an antibiotic together with an inserted antibiotic resistance gene as described above) is by means of the reporter gene β-glucuronidase, the use of which is described below as well as in WO 93/05163.

The resulting transgenic Cyamopsis shoots may then be regenerated into whole plants by known methods, i.e. either by direct root formation on the shoots or by grafting of the transgenic shoots onto established, rooted plants. The latter method, grafting of the transgenic shoots onto the stems of established plants (which themselves may be transgenic or not) has been found to be suitable, resulting in chimeric plants capable of producing transgenic seeds. It has further been found that particularly good results are obtained when transgenic shoots are grafted onto seedlings, e.g. seedlings 7–28 days old, typically 12–21 days old.

As mentioned above, another aspect of the present invention relates to a method for producing a genetically modified plant in which at least one medium used for selection or growth of cells, protoplasts, callus or plant parts comprises a at least one substance that inhibits bacterial growth or that increases the effect of a bacterial growth inhibitor without having any substantial plant growth regulating or plant toxic effect, e.g. a β-lactamase inhibitor. This aspect is related to the fact that the advantageous effect of using e.g. a β-lactamase inhibitor such as sulbactam is not limited to the transformation and selection of guar plants, but rather is generally applicable to Agrobacterium-mediated gene transfer (or in the presence of other β-lactamase producing bacteria strains) in any plant for the purpose of eliminating undesired bacteria growth subsequent to transformation. A significant practical and economic benefit of this approach is that the amount of penicillin-like antibiotics used in the selection and shoot growth media can be greatly reduced, e.g. to a level of about 10% of that which is necessary in the absence of the β-lactamase inhibitor. When the β-lactamase inhibitor is sulbactam, it is used in the amounts given above.

The invention is further illustrated by the following non-limiting examples.

EXAMPLES

General procedure for guar transformation

Seedlings

Guar seeds were sterilized in a sodium chlorite solution containing 2.5% free chlorine, pH 7.0, and two drops of Tween 80 pr. 100 ml of solution. The seeds (about 10 g pr. 100 ml) were stirred for 25 min., washed 5 times with sterile water and dried on filter paper overnight.

The seeds were then sown on germination medium and placed in the dark at 25° C. for 4 days. Then germination was continued at a 12h/12h day/night regime for 7 days. The rich germination medium used resulted in high quality guar seedlings.

Germination medium:

4.43 g/l MSMO (Sigma M6899)

20 g/l sucrose 8.0 g/l agar pH 5.8 (adjusted with KOH)

*Agrobacterium tumefaciens* suspension

The Agrobacterium suspension was prepared as an overnight culture (incubation for 17–18 h) in LB-medium. Acetosyringone was not added to the bacteria culture.

LB-medium:

10 g/l Bacto tryptone 10 g/l NaCl 5.0 g/l yeast extract pH 7.4 (adjusted with NaOH)

Transformation and co-cultivation

The bacteria suspension was in most cases diluted to OD 0.1 (660 nm) with LB-medium, but good results have also been obtained at OD about 1.

Cotyledons with about 2 mm of hypocotyl were excised from 12 day old seedlings. The cotyledons were then torn apart using a tweezers to create wound surfaces and placed in the Agrobacterium-suspension for 30 min.

The preferred procedure for co-cultivation was the so-called sandwich method where the explants were placed on filter paper which in turn was placed on the co-cultivation medium.

Filter paper soaked in liquid co-cultivation medium was also placed on top of the explants in order to prevent the explants from drying.

Co-cultivation medium:

0.43 g/l MS basal salt mixture (Sigma M5524)

20 g/l sucrose 100 mg/l myo-inositol 0.1 mg/l thiamine, HCl 0.5 mg/l pyridoxine, HCl 0.5 mg/l nicotinic acid 1.0 µM silver thiosulfate 8.0 g/l agar pH 5.1

Co-cultivation proceeded for 3 days at 25° C. and a 12 h/12 h day/night regime. After co-culture the explants were washed with 1/10 MS-medium, to which 100 mg/l carbenicillin, 100 mg/l cefotaxime and 1000 mg/l lysozyme had been added, 2–3 times for 45 min. while stirring at 100 rpm.

Selection

The explants were transferred to selection medium and incubated as above (25° C., 12 h day/12 h night).

Selection medium:

3.2 g/l Gamborg B5 (Sigma G5893)

20 g/l sucrose 1.0 mg/l benzylaminopurine 0.05 mg/l gibberellic acid (GA3)

1.0 $\mu$M silver thiosulfate 1.0 mg/l $NiCl_2$, 6 H2O 0.5 mg/l 2-(p-chlorophenoxy)-2-methylpropionic acid (PCIB)

50 mg/l cefotaxime 50 mg/l carbenicillin 100 mg/l sulbactam (Betamaze)

145 mg/l kanamycin sulfate pH 5.7

Harvest of transgenic shoots

First harvest:

After 4 weeks, shoots larger than 3 mm were harvested and transferred to shoot medium. After 10–14 days the shoots were tested for activity of the reporter gene β-glucuronidase (GUS), see below. GUS-positive shoots were transferred to fresh shoot medium while the GUS-negative shoots were discarded.

Shoot medium:

3.2 g/l Gamborg B5 (Sigma G5893)

20 g/l sucrose 0.1 mg/l benzylaminopurine 1.0 AM silver thiosulfate 0.1 mg/l gibberellic acid (GA3)

100 mg/l cefotaxime 100 mg/l sulbactam (Betamaze)

8.0 g/l agar pH 5.7

Second harvest:

After the first harvest, explants (from which shoots had been harvested) were transferred to a second selection medium with a lower kanamycin concentration (50 mg/l). After another 4 weeks shoots were harvested and GUS-tested. The positive shoots were transferred to fresh medium, while the negatives were discarded.

Analysis of transgenic shoots.

Tips of young leaves were excised and transferred to a multi-dish well containing 200 $\mu$l X-gluc solution. After incubation for 16 h at 35° C. the leaf tips were destained with 96%. ethanol and the degree of blue stain was determined under a microscope.

| X-gluc solution (50 ml) | |
|---|---|
| 0.2 M $Na_2HPO_4$ | 15.5 ml |
| 0.2 M $NaH_2PO_4$ | 9.5 ml |
| $H_2O$ | 19.5 ml |
| 0.1 M $K_3(Fe(CN)_6)$ | 0.25 ml |
| 0.1 M $K_4(Fe(CN)_6)$, 3 $H_2O$ | 0.25 ml |
| 0.1 M $Na_2$-EDTA | 5.0 ml |
| X-gluc (cyclohexyl ammonium 5-bromo-4-chloro-3-indolyl-β-D-glucuronate) | 50 mg |

Grafting

Rooting of transgenic shoots was accomplished by grafting. Shoots with a healthy green appearance and with a length of 0.5–1.0 cm were selected for grafting on 1.5–2 month old guar plants grown at a 32° C./25° C. 14 h/10 h day/night regime. Before grafting all leaves except the uppermost two leaves were removed, and the transgenic shoots were grafted onto nearly vertical cuts in the stem at the nodes. The grafted plants were transferred to a humidity chamber for 5–6 days.

Transgenic plants

The grafted plants were subsequently transferred to a growth chamber for further growth of the transgenic shoots. The growth conditions were as above. After about 2 months mature pods with numerous transgenic seeds were harvested.

EXAMPLE 1

Transformation of different varieties of guar

This example shows the transformation of several guar varieties using the above-described method.

| Guar variety | No. of GUS + shoots |
|---|---|
| Lewis | 8 |
| Santa Cruz | 3 |
| Indian | 6 |

The number of GUS+ (GUS-positive, i.e. transformed) shoots is calculated per 1000 explants transformed using the nopaline Agrobacterium strain C58. The American variety Lewis gave the highest number of transgenic shoots harbouring the GUS gene as a marker for successful transformation, and this variety was the one used in the subsequent examples.

EXAMPLE 2

Agrobacteria

A number of different disarmed Agrobacterium tumefaciens strains were tested for transformation of guar, and all were found to be suitable. For example, 500 guar explants pr. bacteria strain were treated with each of four different strains (the octopine strain LBA 4404, Ditta et al., *Proc. Nat. Acad. Sci.* 77: 7347, 1980, and three strains derived from C58). For each strain, 11–26 regenerated shoots, of which 1–3 were GUS-positive shoots, were produced. Similarly, another Agrobacterium strain (the L,L-succinamopine strain EHA 101), which was used to treat 2500 explants, resulted in 25 regenerated shoots, of which 8 were GUS-positive. LBA 4404 was also used to treat 2000 explants, resulting in 67 regenerated shoots, of which 17 were GUS-positive.

The *A. tumefaciens* strains employed contained in the T-DNA region genes encoding β-glucuronidase (for the GUS assay) and neomycin phosphotransferase (for selection on the kanamycin-containing media).

EXAMPLE 3

Kanamycin selection

In this example, the optimal kanamycin sulfate concentration in the selection medium was 145 mg/l, but efficient transformation was also obtained using other concentrations in the range 125–145 mg/l. Using 100 mg/l kanamycin or less gave regeneration frequencies close to 1000, although only very few transgenic shoots were obtained.

| Kanamycin sulf. conc. (mg/l) | No. of regenerated shoots | No. of GUS + shoots |
| --- | --- | --- |
| 125 | 21 | 3 |
| 135 | 19 | 5 |
| 145 | 15 | 8 |

For each treatment a total of 1600 explants were transformed with Agrobacterium strain EHA 101. About 500%. of the transgenic shoots were found at the second harvest, where the kanamycin concentration was reduced. When the kanamycin concentration was maintained at 125–145 mg/l only a few transgenic shoots were found at the second harvest.

EXAMPLE 4

BAP and $NiCl_2$

This example shows the beneficial effects of adding benzyladenine purine (BAP) and $NiCl_2$ to the selection medium.

| BAP (mg/l) | $NiCl_2$, $6H_2O$ (mg/l) | No. of GUS + shoots |
| --- | --- | --- |
| 1.0 | 0 | 1 |
| 1.0 | 1.0 | 4 |
| 5.0 | 0 | 2 |
| 5.0 | 1.0 | 4 |

For each treatment a total of 1200 explants were transformed using Agrobacterium strain EHA 101. Addition of 5 mg/l BAP increased the number of transformants but also the total number of regenerated shoots, which was about twice as high on 5 mg/l BAP as on 1 mg/l.

Addition of 1 mg/l $NiCl_2$, $6H_2O$ resulted in a 2–4 times higher transformation frequency, probably because of the absence of Ni in the employed MS and Gamborg B5 media.

EXAMPLE 5

Silver thiosulfate

This example shows that silver thiosulfate (STS) enhances transformation frequency significantly.

| Conc. of STS ($\mu$M) | No. of GUS + shoots |
| --- | --- |
| 0 | 4 |
| 2.5 | 12 |
| 5.0 | 8 |
| 10.0 | 7 |

The number of GUS+ shoots is calculated per 1000 explants transformed using EHA 101. A concentration of 2.5 $\mu$M silver thiosulfate resulted in significantly more transformants than 0, 5.0 or 10.0 $\mu$M silver thiosulfate.

The increased transformation frequency caused by STS was due to significantly improved shoot quality. In the absence of STS, transgenic shoots were stunted and yellowish, while the presence of STS sustained growth. Since silver ions are known to inhibit the action of ethylene, the beneficial effects of STS could be due to a reduced effect of ethylene in the containers, preventing premature senescence.

EXAMPLE 6

PCIB

PCIB (2-(p-chlorophenoxy)-2-methylpropionic acid) has an anti-auxin effect and can inhibit callus formation. In the absence of PCIB, callus formation was extensive during the selection procedure, impairing regeneration.

Addition of 0.1–2 mg/l PCIB reduced the amount of callus significantly and enhanced regeneration and the number of transgenic shoots.

EXAMPLE 7

Sulbactam

This example shows that the β-lactamase inhibitor sulbactam significantly reduces the amounts of carbenicillin and cefotaxime required for selection and increases transformation frequency.

| Carbenicil. (mg/l) | Cefotaxime (mg/l) | Sulbactam (mg/l) | No. of GUS + shoots |
| --- | --- | --- | --- |
| 800 | 0 | 0 | 2 |
| 100 | 100 | 100 | 5 |
| 50 | 50 | 100 | 9 |

For each treatment a total of 800 explants were transformed using EHA 101. All 3 treatments resulted in elimination of Agrobacteria.

Transgenic shoots on 800 mg/i carbenicillin grew poorly and had a yellowish appearance. These shoots did not recover after transfer to the shoot medium, and many transgenic shoots eventually died.

Transgenic shoots selected on 50 or 100 mg/l carbenicillin in the presence of 100 mg/l sulbactam grew well, had a normal green appearance and could be maintained in vitro for extended periods.

EXAMPLE 8

Thidiazuron

Addition of the cytokinin thidiazuron (TDZ) significantly enhanced transformation frequencies. As shown in the table below the optimum TDZ concentrations in the selection media were in the range of 0.3–3.0 mg/l, which increased the transformation frequencies 1.5–1.8 fold.

| Thidiazuron (mg/l) | No. of explants | No. of GUS + shoots | Transform. freq. (%) |
| --- | --- | --- | --- |
| 0 | 5076 | 34 | 0.67 |
| 0.3 | 742 | 8 | 1.08 |
| 1.0 | 741 | 9 | 1.21 |
| 3.0 | 1522 | 16 | 1.05 |
| 4.5 | 797 | 5 | 0.63 |

In addition to increasing transformation frequency, thidiazuron was also beneficial for the subsequent cloning of the transgenic shoots.

EXAMPLE 9

Grafting

Rooting of the transgenic shoots was accomplished by grafting. Although grafting on developed plants (1.5–2 months old) is possible, as explained above, even better success rates were obtained by grafting onto seedlings which were 12–21 days old.

The seedlings were produced by placing sterilized guar seeds on germination medium (vide supra) and subsequently culturing them for 12–21 days at 25° C. at a 13h/11 h day/night regime. The cotyledons were excised and the hypocotyl was cut vertically 0.5–1 cm down. A transgenic shoot was placed in the incision and fastened with a short piece of sterile string. After 5–10 days the string was removed and the grafted plantlets were transferred to soil.

Out of 49 transgenic shoots grafted onto such seedlings, 42 survived (89%) and resulted in fertile plants with a normal phenotype.

EXAMPLE 10

Southern blot analysis

In order to confirm the presence of the transgenes and the gene copy number in transgenic guar lines genomic DNA was extracted from leaf samples, digested with HindIII and subjected to electrophoresis on a 0.8% agarose gel. Southern blots were done with Hybond N+ (Amersham) and prehybridization and hybridization was at 68° C. in the buffer recommended by the manufacturer. DNA probes were either the PMI gene or the GUS gene labelled by random priming with the "Ready to go" kit (Pharmacia). $1 \times 10^6$ CPM/ml of labelled probe was added to the hybridization buffer.

The Southern blot analysis using the PMI gene as a probe is shown in FIG. 1. As can be seen each lane, except lane 1, shows an intense band at 2.1 kb, which is the expected size of the DNA fragment obtained by digestion by HindIII. Lane 1 shows a faint band of a similar size. Lane 8 is a non-transgenic guar line.

The Southern blot analysis using the GUS gene as a probe is shown in FIG. 2. As can be seen most of the lanes show one intense band, indicating that these lines contain one copy of the GUS gene. The digestion of the DNA in lane 7 has resulted in 4 bands, suggesting that this line contains 4 copies of the GUS gene. Lane 8 is a non-transgenic guar line.

EXAMPLE 11

Analysis of transgenic offspring

Figure 1:
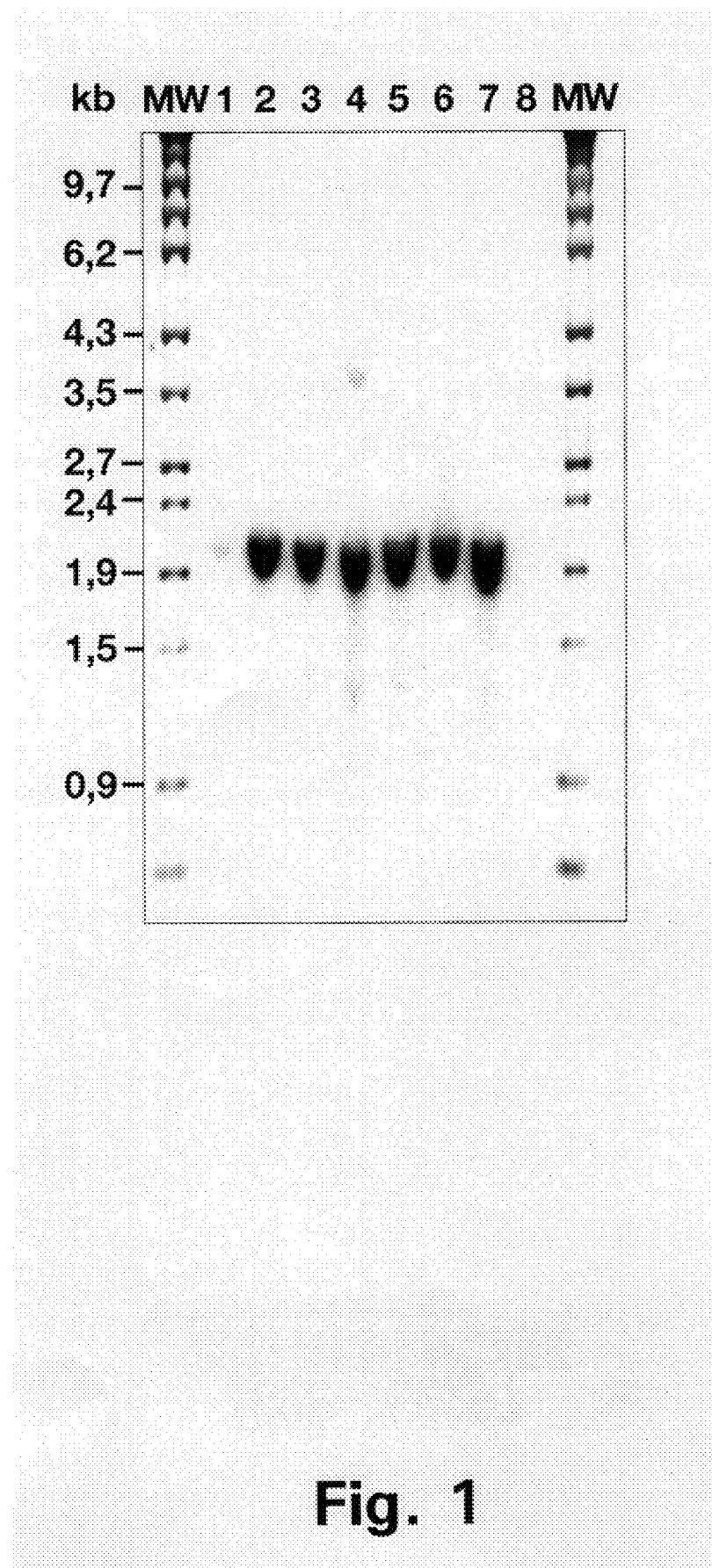
FIG. 1 shows genomic Southern analysis of transgenic guar lines. 10 μg genomic DNA of different transgenic guar lines digested with HindIII was subjected to electrophoresis on a 0.8% agarose gel and the DNA was blotted onto Hybond N+ and hybridized to a probe consisting of the PMI gene labelled with [$^{32}$P]dCTP. [$^{35}$S] DNA markers (Amersham) were used as a molecular weight marker (MW).
Figure 2:
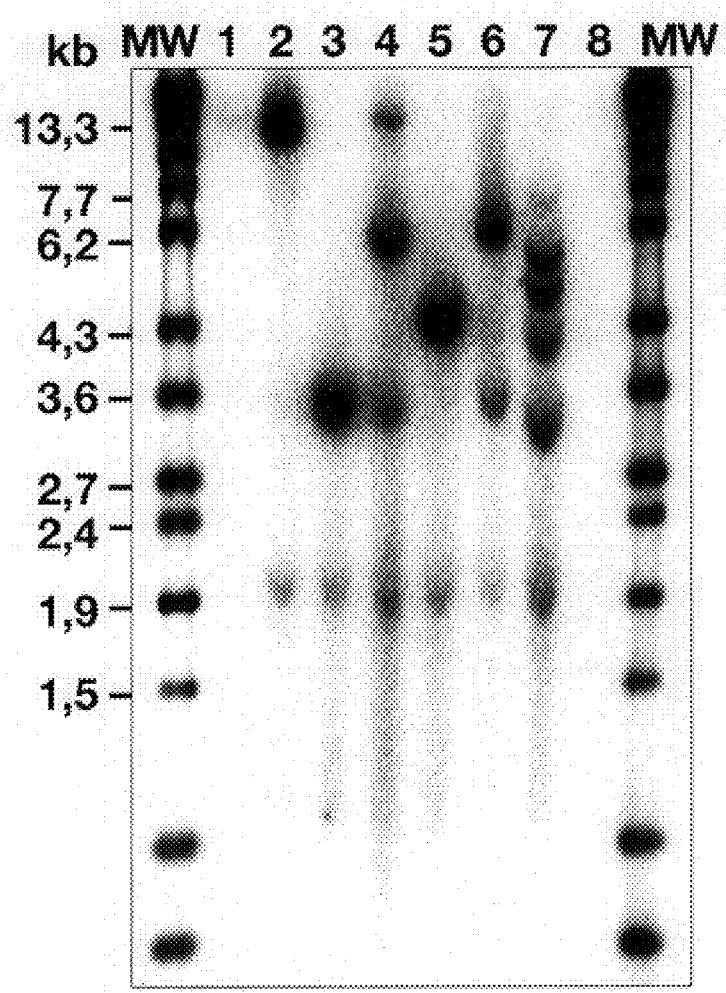
FIG. 2 shows genomic Southern analysis of transgenic guar lines. 10 μg genomic DNA of different transgenic Guar lines digested with HindIII was subjected to electrophoresis on a 0.8% agarose gel and the DNA was blotted onto Hybond N+ and hybridized to a probe consisting of the GUS gene labelled with [$^{32}$P]dCTP. [$^{35}$S]DNA markers (Amersham) were used as a molecular weight marker (MW).

Inheritance and segregation of the transgenes was studied in some of the independent guar transformants. Primary transformants were self-fertilized and a number of seeds (10–20) were sown. The presence of GUS gene in the second generation plants was demonstrated by the GUS-assay (vide supra).

| Transformant no. | No. of seeds sown | No. of GUS positive | No. of GUS negative | % GUS positive |
| --- | --- | --- | --- | --- |
| P16 | 20 | 11 | 9 | 55% |
| P18 | 20 | 12 | 8 | 60% |
| P31 | 10 | 7 | 3 | 70% |

This table shows that the GUS gene is inherited in a stable manner and that it segregates approximately as would be expected for a single dominant gene. Furthermore, the GUS gene has retained its activity.

What is claimed is:

1. A method for producing a genetically modified plant or part thereof of the genus Cyamopsis, comprising the steps of introducing a recombinant DNA sequence into at least one cell or protoplast by means of a β-lactamase producing agrobacterium and generating genetically modified explants using at least one selection or shoot growth medium comprising (a) at least one β-lactamase inhibitor and (b) at least one auxin inhibitor or ethylene inhibitor, so as to obtain a genetically modified plant or part thereof containing in its genome at least one recombinant DNA sequence.

2. A method according to claim 1 wherein genetically modified shoots are generated using a selection medium comprising at least an auxin inhibitor and a β-lactamase inhibitor, and a shoot growth medium comprising at least a β-lactamase inhibitor.

3. A method according to claim 2, wherein the selection medium comprises an auxin inhibitor, a β-lactamase inhibitor and an ethylene inhibitor, and the shoot growth medium comprises an auxin inhibitor and an ethylene inhibitor.

4. A method according to claim 1 wherein the auxin inhibitor is 2- (p-chlorophenoxy) -2-methylpropionic acid (PCIB) and the β-lactamase inhibitor is sulbactam.

5. A method according to claim 1 wherein the selection medium comprises PCIB as the auxin inhibitor in a concentration of 0.01–10 mg/l and sulbactam as the β-lactamase inhibitor in a concentration of 10–1000 mg/l, and the shoot growth medium comprises sulbactam as the β-lactamase inhibitor in a concentration of 10–1000 mg/l.

6. A method according to claim 5 wherein the selection medium comprises PCIB in a concentration of 0.05–5 mg/l.

7. A method according to claim 5 wherein the selection medium and/or the shoot growth medium comprises sulbactam in a concentration of 20–500 mg/l.

8. A method according to claim 1 wherein the selection medium comprises kanamycin sulfate in a concentration of 50–300 mg/l.

9. A method according to claim 8 wherein explants are transferred from the selection medium to a second selection medium comprising kanamycin sulfate in a concentration lower than that of the first selection medium.

10. A method according to claim 1 wherein the selection and/or shoot growth medium comprises silver thiosulfate as the ethylene inhibitor in a concentration of up to 50 μM.

11. A method according to claim 10 wherein the selection and/or shoot growth medium comprises silver thiosulfate in a concentration of 0.1–10 μM.

12. A method according to claim 1 wherein the selection and/or shoot growth medium further comprises a nickel salt.

13. A method according to claim 1 wherein the selection and/or shoot growth medium further comprises a gibberellin.

14. A method according to claim 1 wherein the selection and/or shoot growth medium further comprises a penicillin-like antibiotic.

15. A method according to claim 1 wherein transformation is performed on cotyledons.

16. A method according to claim 15 wherein the cotyledons are from seeds that have been germinated for at least 4 days.

17. A method according to claim 1 for producing a genetically modified plant of the species *C. tetragonoloba*.

18. A method according to claim 9 wherein the kanamycin sulfate concentration in the second selection medium is not more than about 125 mg/l.

19. A method according to claim 14 wherein the penicillin-like antibiotic is selected from carbenicillin and cefotaxime.

20. A method according to claim 16 wherein the cotyledons are from seeds that have been germinated for at least 7 days.

21. A genetically modified plant or part thereof of the genus Cyamopsis produced by the method of claim 1.

22. A method for producing a genetically modified plant or part thereof of the genus Cyamopsis, comprising the steps of introducing a recombinant DNA sequence into at least one cell or protoplast by means of a β-lactamase producing agrobacterium and generating genetically modified explants using at least one selection or shoot growth medium comprising a nickel salt, so as to obtain a genetically modified plant or part thereof containing in its genome at least one recombinant DNA sequence.

23. The method of claim 1 wherein the selection medium comprises (a) at least one beta-lactamase inhibitor and (b) at least one auxin inhibitor or ethylene inhibitor.

24. The method of claim 1 wherein the shoot growth medium comprises (a) at least one beta-lactamase inhibitor and (b) at least one auxin inhibitor or ethylene inhibitor.

25. The method of claim 1 which the selection or shoot growth medium comprises at least one beta-lactamase inhibitor and at least one auxin inhibitor.

26. The method of claim 1 in which the selection or shoot growth medium comprises at least one beta-lactamase inhibitor and at least one ethylene inhibitor.

27. The method of claim 26 in which the selection or shoot growth medium comprises at least one auxin inhibitor.

28. A method for producing a genetically modified plant or part thereof of the genus *Cyamopsis*, comprising the steps of introducing a recombinant DNA sequence into at least one cell or protoplast by means of a β-lactamase producing Agrobacterium and generating genetically modified explants using at least one selection or shoot growth medium comprising at least one β-lactamase inhibitor.

29. The method of claim 28 where said medium further comprises benzyladenine purine.

30. The method of claim 28 where said medium further comprises the cytokinin thidiazuron.

* * * * *